US006616637B2

(12) United States Patent
Alexander et al.

(10) Patent No.: US 6,616,637 B2
(45) Date of Patent: Sep. 9, 2003

(54) FLUID COLLECTION SAFETY SYRINGE

(76) Inventors: Gary E. Alexander, 6244 Krista La., Baton Rouge, LA (US) 70808; Thomas John, 10641 N. Oak Hills Pkwy., Baton Rouge, LA (US) 70810

( * ) Notice: Subject to any disclaimer, the term of this patent is extended or adjusted under 35 U.S.C. 154(b) by 0 days.

(21) Appl. No.: 09/864,612

(22) Filed: Aug. 5, 2002

(65) Prior Publication Data

US 2002/0183697 A1 Dec. 5, 2002

Related U.S. Application Data

(63) Continuation of application No. 09/598,623, filed on Jun. 21, 2000, now abandoned.

(51) Int. Cl.[7] ............................................. A61M 5/32
(52) U.S. Cl. ..................................................... 604/192
(58) Field of Search ............................ 604/195, 187, 604/196, 192, 197, 198, 199, 905

(56) References Cited

U.S. PATENT DOCUMENTS

| | | | | |
|---|---|---|---|---|
| 4,767,413 A | * | 8/1988 | Haber et al. ................ 604/198 |
| 4,946,446 A | * | 8/1990 | Vadher ........................ 604/198 |
| 5,873,856 A | * | 2/1999 | Hjertman et al. ............ 604/117 |
| 5,935,113 A | * | 8/1999 | Dysarz ........................ 604/263 |
| 6,217,559 B1 | * | 4/2001 | Foster ......................... 604/195 |
| 6,379,336 B1 | * | 4/2002 | Asbaghi et al. ............. 604/192 |

* cited by examiner

*Primary Examiner*—Manuel Mendez
(74) *Attorney, Agent, or Firm*—Roy, Kiesel, Keegan and DeNicola

(57) ABSTRACT

A safety syringe for a vacuum specimen tube having a stopper. The syringe includes a shroud with a double ended needle and a sheath slidably positioned over the needle's external end. The sheath's tip can be hypodermically inserted with the needle. The sheath moves between an exposed position where the sharp point of the needle's external end is exposed and a covered position where the sharp point of the needle's external end is inside the sheath. After the needle and sheath are inserted into the patient, the vacuum tube is seated in the shroud, piercing the stopper with needle's internal end and allowing blood to flow into the tube. As the tube is seated, it will also preferably engage an arm extending from the sheath to advance the sheath into the covered position. Thus, the sheath is in the covered position before the syringe is removed from the patient.

20 Claims, 7 Drawing Sheets

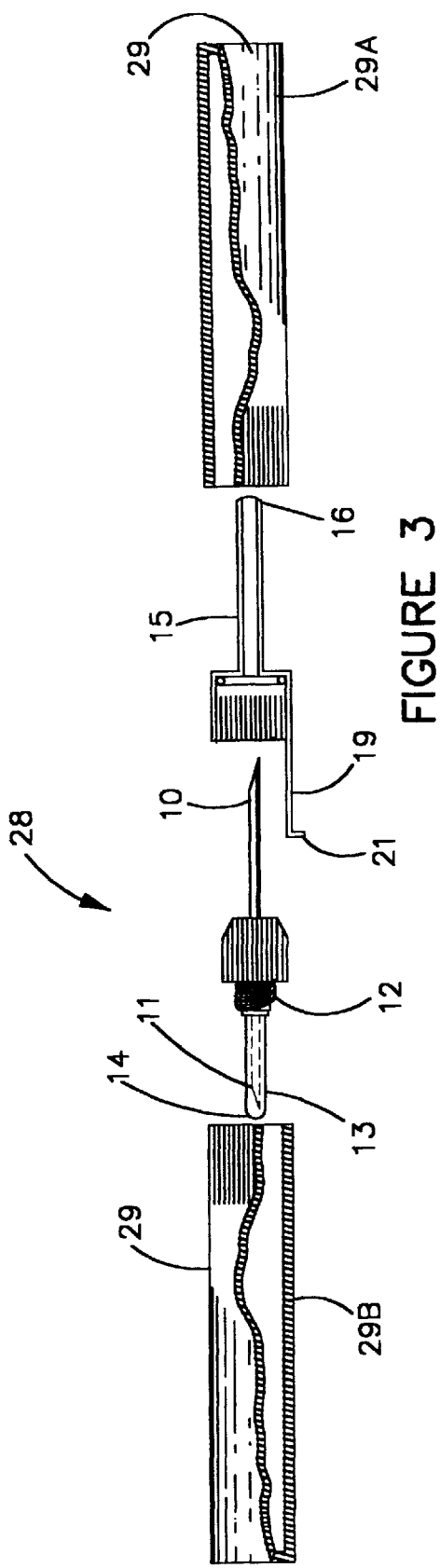

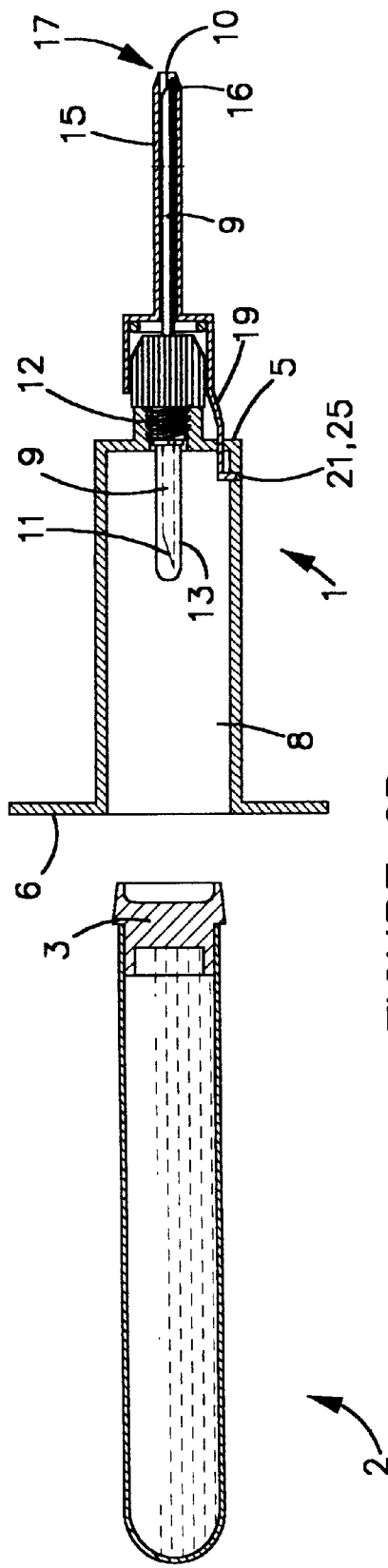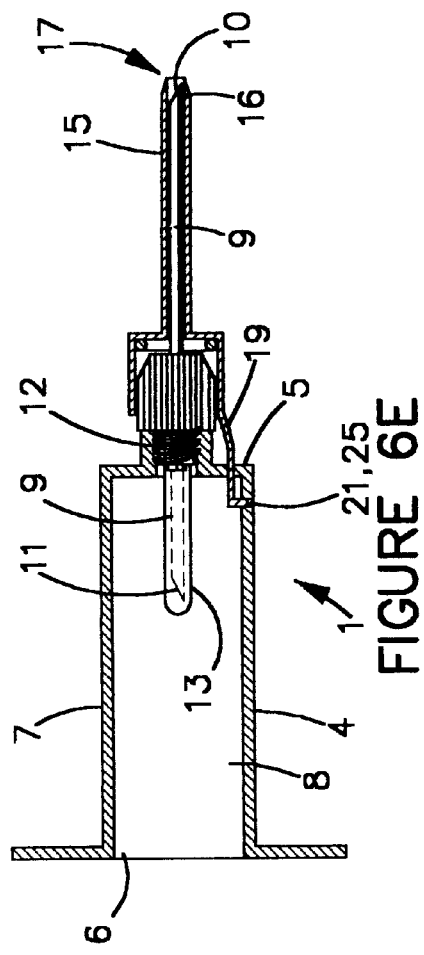
FIGURE 6D
FIGURE 6E

FLUID COLLECTION SAFETY SYRINGE

PRIORITY INFORMATION

This is a continuation of U.S. patent application Ser. No. 09/598,623, filed Jun. 21, 2000, now abandoned, which is hereby incorporated by reference in its entirety.

BACKGROUND OF THE INVENTION

1. Field of the Invention

The invention relates to safety syringes in general and to blood collection safety syringes in particular.

2. Prior Art

The risk of contracting diseases such as HIV or hepatitis from accidental sticks with dirty needles is a potentially deadly hazard for medical professionals. One of the most dangerous times for accidental sticks is during blood collection. This is frequently done with a syringe and one or more vacuum specimen tubes. These syringes are typically comprised of a hollow shroud having an open end and a closed end. A double pointed hollow needle is usually threaded into the closed end of the shroud such that one end of the needle is positioned outside of the shroud and the other end of the needle is positioned inside the shroud. Both ends of the needle are usually sharp. The end of the needle that is inside the shroud is usually covered with a collapsible latex sleeve which seals the end of the needle.

The vacuum specimen tubes are essentially test tubes sealed with a rubber stopper. These tubes are usually sealed under a vacuum but in their principal intended use, they only require a pressure that is lower than the venous pressure of the patient in order to draw blood. Thus, as used herein the term "vacuum specimen tube" refers to sealed tubes having an internal pressure that is less than the venous pressure of the patient.

In operation, the external end of the needle is injected into the patient, usually into a vein. At this point, the collapsible sleeve prevents blood from flowing out of the needle. A vacuum specimen tube will then be inserted into the open end of the shroud until the rubber stopper encounters the internal end of the needle. Continued application of pressure to the vacuum specimen tube will cause the sharp point of the internal end of the needle to pierce the collapsible sleeve and enter the rubber stopper. When the stopper has been completely pierced, the needle will provide fluid passage between the vein and the vacuum specimen tube. The difference in pressure between the tube and the vein will cause blood to flow into the tube until the pressure is equalized. When this happens, the tube will usually be removed while the needle is still in the patient. The sleeve will snap back into place when the tube is removed. Even though the sleeve has been pierced, it is resilient enough to prevent blood from escaping while the tube is out of place. If more blood is required, a fresh tube may be placed onto the internal end of the needle. This is repeated until the desired amount of blood has been collected.

When the last tube has been filled, the needle is removed from the patient. At this time, the needle is dirty and exposed and an accidental stick is possible from this point on. This may occur while the medical professional is removing the last tube from the syringe or while she is disposing the syringe. Also, personnel handling medical refuse may be stuck after the syringe has been discarded.

The foregoing description assumes that the patient is well behaved and that blood is drawn in a careful and orderly fashion. All too frequently, this is not the case. In many emergency room settings, such as trauma or overdose cases, the patient may be violent, and he may need to be restrained in order for blood to be drawn. Children may also behave uncontrollably during blood collection. Such activity on the part of the patient obviously increases the risk of an accidental stick. It also changes the time when protection is required. In a case where the patient is orderly and all goes well, protection from an accidental stick is not needed until after blood collection is complete. Where the patient is disorderly, protection is required during the collection procedure.

Protection during the collection procedure is also beneficial for the patient. He is exposed to potential injury while the sharp needle is in his vein. If the patient becomes agitated, his movements may cause the needle to damage the vein or the surrounding tissue. Even if the patient is still, the movement of the syringe by the medical professional as she is changing tube may cause damage to the vein. Accordingly, a safety syringe that meets the following objectives is desired.

OBJECTS OF THE INVENTION

It is an object of the invention to help prevent the transmission of AIDS and other diseases through accidental sticks with contaminated needles.

It is an object of the invention to provide a safety syringe which minimizes the chances of an accidental stick with a contaminated needle.

It is an object of the invention to provide a safety syringe which minimizes the risk of damage to the veins of the patient.

It is an object of the invention to provide a safety syringe capable of collecting blood and other fluids.

It is another object of the invention to provide a safety syringe in which the needle is covered prior to its removal from the patient.

It is yet another object of the invention to provide a safety syringe in which the sheath is locked into place when the needle is covered.

It is still another object of the invention to provide a safety syringe that operates in a substantially similar fashion to a conventional blood collection syringe.

SUMMARY OF THE INVENTION

The invention is a safety syringe for collecting fluids in a vacuum specimen tube. The syringe comprises a shroud having a first end, a second end, and sidewalls extending therebetween, all of which define a shroud chamber. The second end is preferably open to provide access to the shroud chamber. The shroud chamber is sized to receive a vacuum specimen tube. A needle having a first end and a second end is mounted in the first end of the shroud such that the first end of the needle is outside of the shroud and the second end of the needle is positioned within the shroud chamber. A blunt sheath having a tip end is slidably disposed over the needle. Preferably, at least the tip end of the sheath is sized to be hypodermically inserted with the first end of the needle. The sheath has a covered position in which the point of the first end of the needle is contained within the sheath. The sheath also has an exposed position in which the point of the first end of the needle is outside of the sheath. The sheath is configured to advance from the exposed position to the covered position by sliding along the needle. Preferably, an arm extends from the sheath to within the shroud chamber. This arm has a tube end opposite the sheath. As the vacuum specimen tube is advanced toward the first end of the needle, the tube will engage the tube end of the arm and push it forward. This will cause the sheath to move from the exposed position to the covered position. This is preferably accomplished immediately after the needle has been inserted into the patient, so that the needle is in the covered position throughout most of the fluid collection procedure, and substantially all the time the needle is dirty.

As the vacuum specimen tube is advanced toward the first end of the shroud, it will also encounter the second end of the needle. The second end of the needle is configured to pierce the stopper sealing the vacuum specimen tube, preferably with a sharp point identical to that of the first end of the needle. When the second end has pierced the stopper, the needle will provide fluid passage into the vacuum specimen tube. At this point, the first end of the needle should already be in the vein or other vessel. If so, the vacuum of the tube will cause fluid to flow through the needle into the tube. When the vacuum specimen tube is full, it may be removed and another added until the desired amount of blood or other fluid has been collected. When the collection is complete and the syringe is removed, it will already be in the covered position.

BRIEF DESCRIPTION OF THE DRAWINGS

FIG. 3 is an exploded view of a preferred embodiment of the needle assembly, including a partial cut away of the both halves of the cap, a side view of the needle and sleeve, and a side cut away view of the sheath.

FIG. 6D is the same view shown in FIG. 6C with the vacuum specimen tube removed from the second end of needle and the sleeve returned to its original position covering the second end of the needle.

FIG. 6E is the same view shown in FIG. 6D with the safety syringe removed from the patient.

DESCRIPTION OF THE BEST MODE OF THE INVENTION

Figure 1:
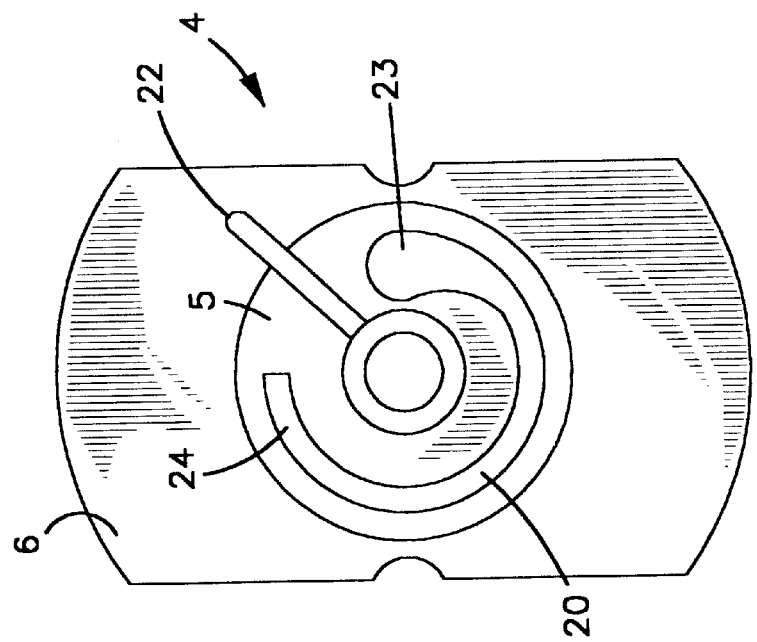
FIG. 1 is a first end view of a preferred embodiment of the shroud.
Figure 2:
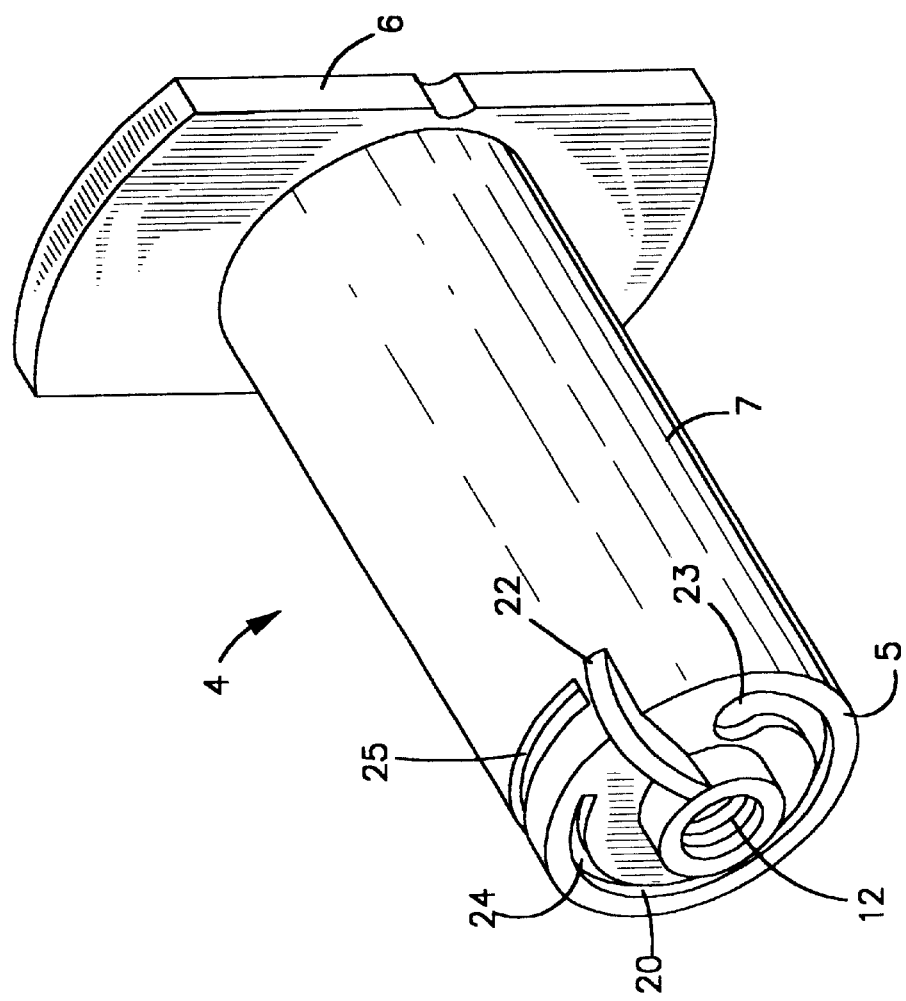
FIG. 2 is a first end view of a preferred embodiment of the shroud.
Figure 4A:
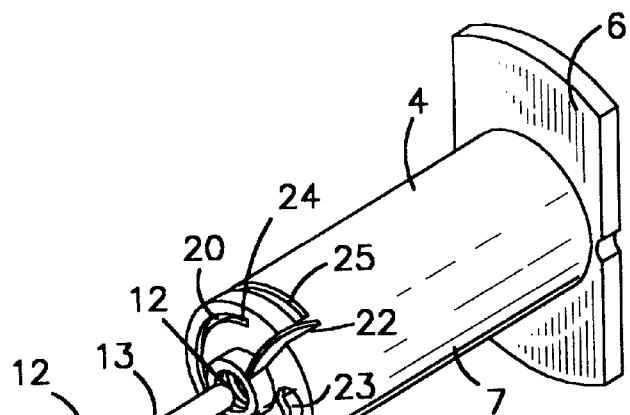
FIGS. 4A–4C are partially transparent perspective views of a preferred embodiment of the safety syringe illustrating the attachment of the needle assembly to the shroud using a Leur lock.
Figure 4B:
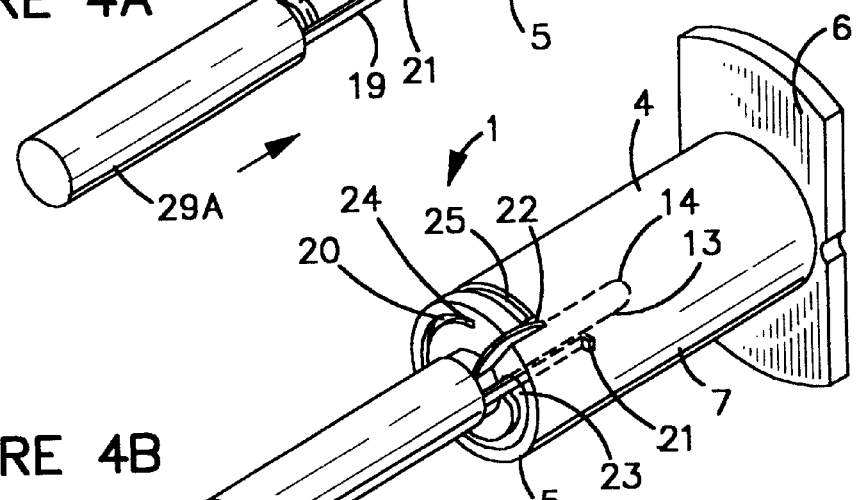
Figure 4C:
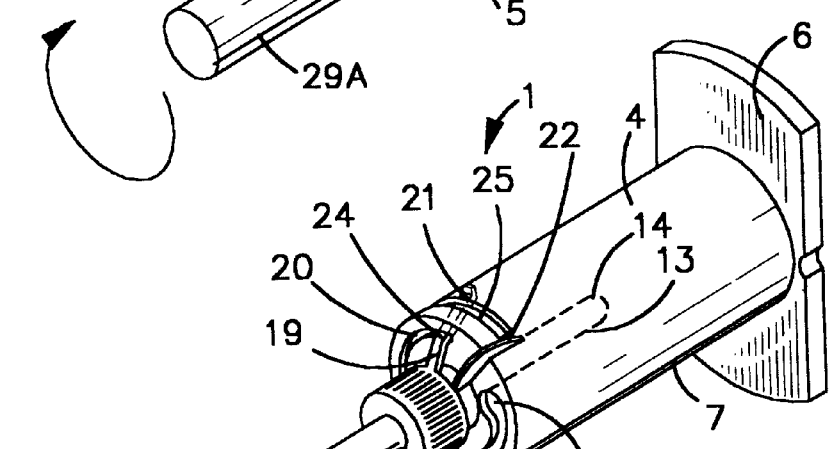
Figure 5A:
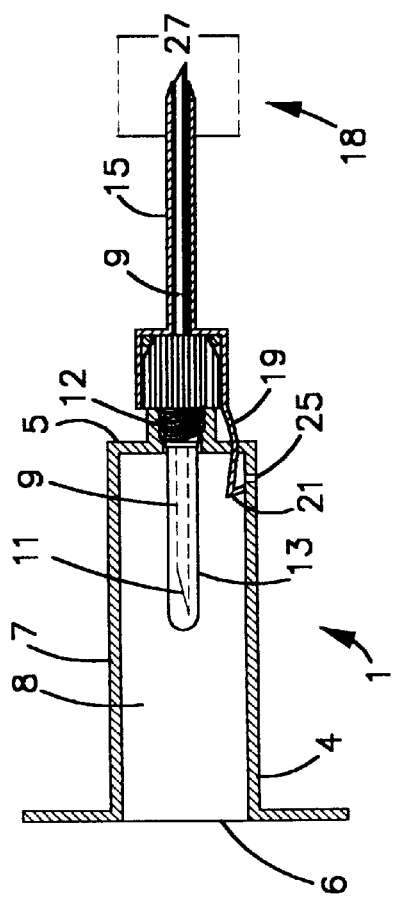
FIG. 5A is a cross sectional view of a preferred embodiment of the safety syringe prior to insertion into a patient with the sheath in the exposed position.
Figure 5B:
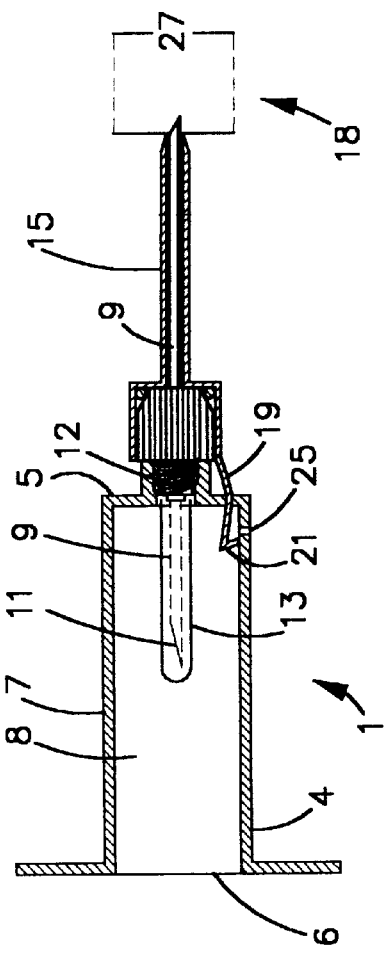
FIG. 5B is the same view shown in FIG. 5A, after the patient has been injected.
Figure 6A:
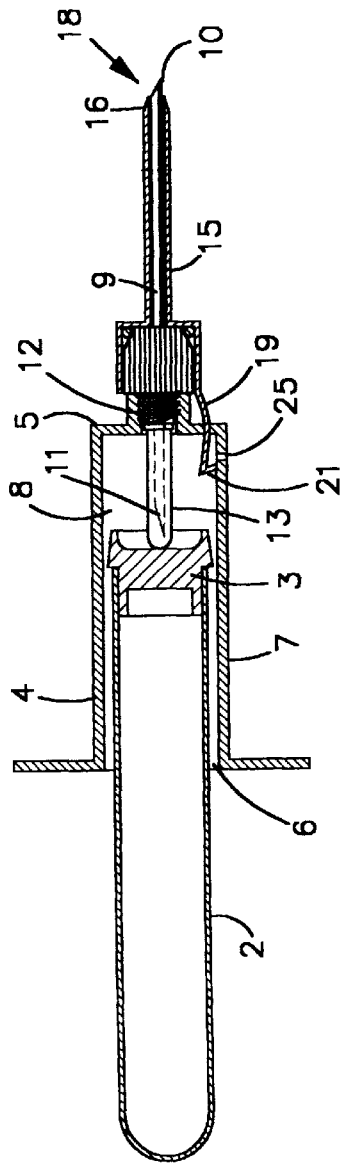
FIG. 6A is a cross sectional view of a preferred embodiment of the safety syringe after injection illustrating the advancement of a vacuum specimen tube into the shroud.
Figure 6B:
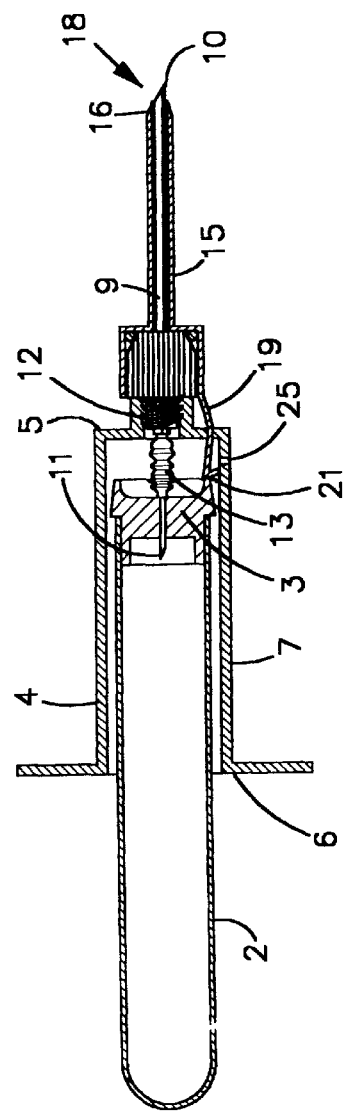
FIG. 6B is the same view shown in FIG. 6A with the vacuum specimen tube advanced to the point that the second end of the needle has pierced the stopper allowing fluid to flow into the vacuum specimen tube and to the point that the arm and the sheath have been engaged by the stopper and moved forward.
Figure 6C:
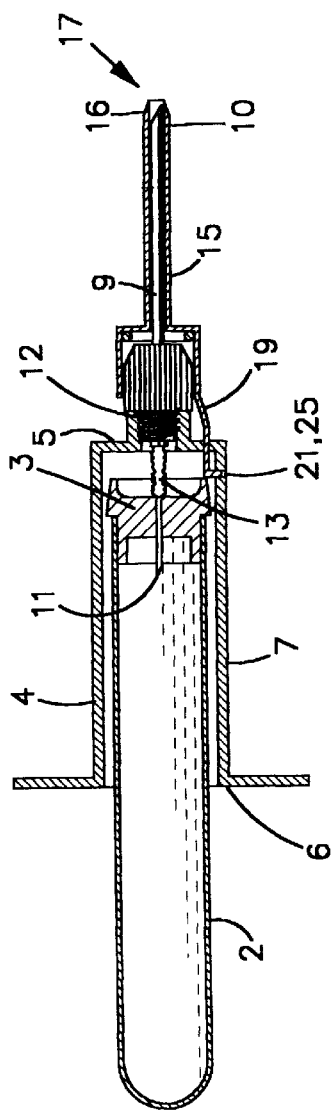
FIG. 6C is same view shown in FIG. 6A with the vacuum specimen tube fully advanced so that the sheath has moved into the covered position and the arm has moved into the recess in the sidewall, locking the sheath in place.
Figure 7A:
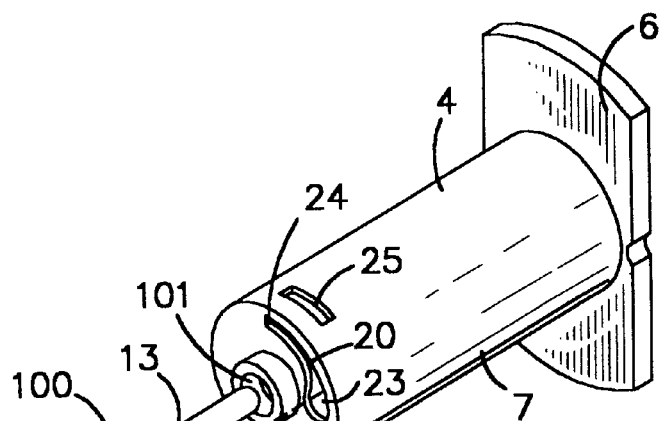
FIGS. 7A–7C are partially transparent perspective views of a preferred embodiment of the safety syringe illustrating the attachment of the needle assembly to the shroud using a friction fit.
Figure 7B:
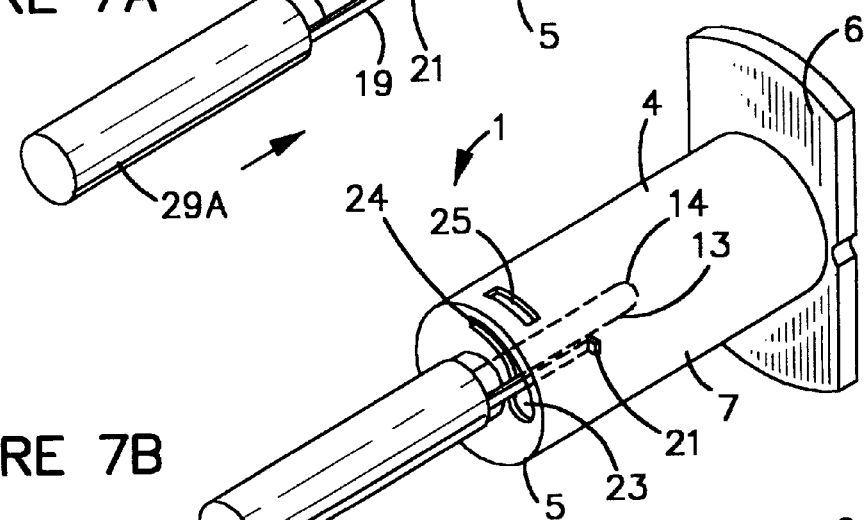
Figure 7C:
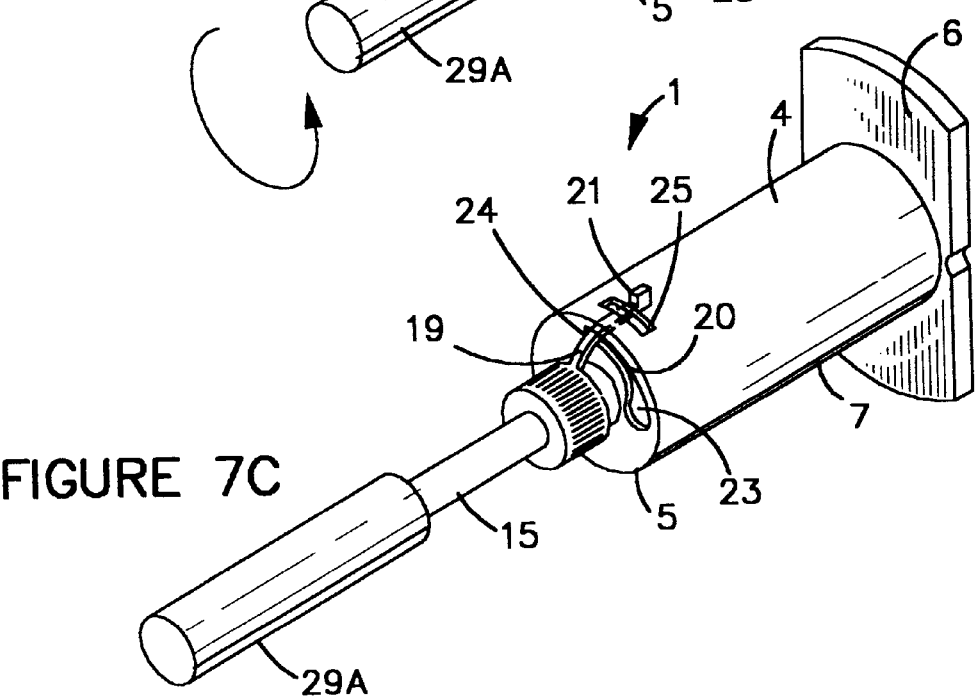

The invention is a safety syringe 1 for use with one or more vacuum specimen tubes 2, preferably sealed with a stopper 3. Syringe 1 comprises a shroud 4 having a first end 5, a second end 6, and sidewalls 7 extending therebetween. First end 5, second end 6, and sidewall s 7 define a shroud chamber 8. Second end 6 is preferably open in order to provide access to shroud chamber 8. Shroud chamber 8 is sized to receive vacuum specimen tube 2.

A needle 9 having a first end 10 and a second end 11 is mounted in first end 5 of shroud 4. Needle 9 should be positioned such that first end 10 of needle 9 is located outside of shroud 4 while second end 11 of needle 9 is contained within shroud chamber 8. Needle 9 may be permanently attached to shroud 4 or it may be releasably attached. In a preferred embodiment, needle 9 is releasably attached to shroud 4 via a Luer lock 12. Luer lock 12 will facilitate the use of needles 9 of varying diameters with a single configuration of shroud 4. In a more preferred embodiment, the threads of Luer lock 12 require a rotation of 180° to 270° and provide for approximately ⅛ of an inch vertical movement of needle 9 relative to shroud 4, the vertical dimension of shroud 4 being the direction parallel to the length of needle 9.

In another preferred embodiment, needle 9 is releasably attached to shroud 4 via friction fit. This is accomplished by providing a taper to the male member 100 of the needle 9. The small portion of male member 100 will be sized to allow male member 100 to enter the female opening 101 in shroud 4. The outside diameter of the largest portion of male member 100 will be approximately equal to the inside diameter of the female opening 101. By rotating needle 9 and male member 100 as male member 100 is inserted into female opening 101, male member 100 may be seated in female opening 101 in a tight fashion, thereby obtaining a seal between male member 100 and female opening 101.

Second end 11 of needle 9 is preferably covered with a collapsible sleeve 13. Collapsible sleeve 13 should be sealably mounted over needle 9 so as to prevent flow through needle 9 until sleeve 13 is punctured. The seal can be created by mounting sleeve 13 to the portion of Luer lock 12 attached to needle 9, when that embodiment is used. Sleeve 13 is preferably made of latex or other similar resilient material. In a preferred embodiment, sleeve 13 is clear or opaque, and in a more preferred embodiment, it has a reservoir tip 14. In this embodiment, the person administering the injection will be able to see when reservoir tip 14 fills with blood, thereby allowing her to tell when a vein has been struck. When vacuum specimen tube 2 is advanced toward first end 5 of shroud 4, it will press sleeve 13 into second end 11 of needle 9. Second end 11 of needle 9 should be configured to pierce sleeve 13 when sleeve 13 is pressed against it. This is preferably done by providing second end 9 with a sharp point. As vacuum specimen tube 2 is advanced further toward first end 5 of shroud 4, second end 11 of needle 9 will pierce stopper 3, preferably with the same sharp point discussed above. As stopper 3 is moved along needle 9, it will push sleeve 13 back toward first end 5 of shroud. When vacuum specimen tube 2 is removed, sleeve 13 should be sufficiently resilient to return to its original position covering second end 11 of needle 9, and to prevent the flow of blood or other fluid through needle 9.

A blunt sheath 15 having a tip end 16 is slidably positioned over needle 9. Sheath 15 or at least tip end 16 are preferably configured to be hypodermically insertable with needle 9. Sheath 15 has a covered position 17 where the point of first end 10 of needle 9 is contained within sheath 15 and an exposed position 18 where the point of first end 10 of needle 9 is outside sheath 15. Sheath 15 is configured to be advanced from said exposed position 18 to said covered position 17 after first end 18 of needle 9 and preferably tip end 16 of sheath 15 have been hypodermically inserted into the patient. This is preferably accomplished by the advancement of vacuum specimen tube 2 toward first end 5 of shroud 4. However, in an alternative embodiment, sheath 15 may be operatively connected to a push-tab (not shown) which may be used by the operator of safety syringe 1 to manually advance sheath 15 into covered position 17.

An arm 19 preferably depends from sheath 15 through a slot 20 in first end 5 of shroud 4. Arm 19 is provided with a tube end 21 opposite sheath 15 which is contained within shroud chamber 8. As vacuum specimen tube 2 is advanced toward first end 5 of shroud 4, it will engage tube end 21 of arm 19 and advance it toward first end 5 of shroud 4. This will advance sheath 15 from exposed position 18 to covered position 17.

In one preferred embodiment, slot 20 is curved in an arc of approximately 270°. Depending on the thickness of shroud 4, slot 20 may leave first end 5 of shroud 4 somewhat weakened. This can be countered in several ways such as using a heavier plastic or providing first end 5 with a brace 22 across the remaining 90° of first end 5.

Slot 20 should preferably have a wide end 23 and a narrow end 24. In this embodiment, tube end 21 should preferably be wider than arm 19. Wide end 23 of slot 20 should be wide enough to allow tube end 21 to pass, but narrow end 24 should not allow tube end 21 to pass. Thus, sheath 15 may be inserted with needle 9 by inserting tube end 21 of arm 19 through wide end 23 of slot 20 and then rotating sheath 15 with needle 9 as needle 9 is threaded onto Luer lock 12. Slot 20 will allow arm 19 to rotate until tube end 21 is in line with narrow end 24 of slot 20. Narrow end 24 will prevent sheath 15 from being removed from needle 9 when arm 19 is in this position.

In another preferred embodiment, arm 19 is configured to bias tube end 21 against sidewalls 7. This may be effected by angling arm 19 relative to sheath 15 such that arm 19 must be bent to position tube end 21 within shroud 4 when sheath 15 is positioned over needle 9. In this embodiment, sidewalls 7 contain a recess 25. Recess 25 should be sized to engage tube end 21 of arm 19. Recess 25 may extend completely through sidewalls 7, or it may only form an indentation. In either case, the tension of arm 19 will push tube end 21 into recess 25 when tube end 21 advances to recess 25. Recess 25 should be positioned so that sheath 15 will have already entered covered position 17 when tube end 21 reaches recess 25. When tube end 21 has engaged recess 25, recess 25 will prevent arm 19 from advancing or retracting, which in turn will prevent sheath 15 from advancing or retracting, thereby locking sheath 15 in covered position 17. Alternatively, the same result could be achieved by replacing recess 25 with a beveled locking detent (not shown) or other equivalent mechanisms.

Recess 25 should preferably be approximately vertically aligned with narrow end 24 of slot 20, when that embodiment is used. Thus, tube end 21 of arm 19 will be aligned with recess 25 when needle 9 has been threaded onto Luer lock 12 and arm 19 has been rotated the length of slot 20. Arm 19, tube end 21, sheath 15, first end 10 of needle 9, and recess 25 should be sized relative to each other so that when needle 9 and sheath 15 are threaded onto Luer lock 12, the $1/8$ inch downward vertical movement provided will place tube end 21 below recess 25 relative to first end 5 of shroud 4, and sufficiently distant from recess 25 to allow sheath 15 to be advanced to covered position 17 before tube end 21 reaches recess 25.

In a preferred embodiment, sheath 15 is sized to be hypodermically insertable with needle 9. Needle 9 will have an external diameter 26. Likewise, sheath 15 will have an external diameter 27. While preferred embodiments of both needle 9 and sheath 15 are generally cylindrical, it is recognized that both may have other shapes such that their cross section is not a circle. In such cases, diameter is intended herein to refer to the longest cross sectional dimension of the respective article unless otherwise indicated. External diameter 27 of sheath 15 at tip end 16 should be close enough to external diameter 26 of needle 9 to allow tip end 16 of sheath 15 to be inserted with needle 9 when safety syringe 1 is used to administer an injection. As needle 9 is inserted into tissue, it will create a puncture wound or tear in that tissue that is somewhat larger in diameter than external diameter 26 of needle 9. Sheath 15, and particularly tip end 16 should be sized to permit at least tip end 16 of sheath 15 to be inserted simultaneously with needle 9 into the puncture wound created by needle 9 during hypodermic injection.

In designing sheath 15, there are two competing goals, strength or puncture resistance and patient comfort. The thinner sheath 15 is, the more comfortable it will be for the patient when sheath 15 is inserted with needle 9 during injection, assuming the hypodermically insertable version of sheath 15 is in use. However, as sheath 15 is made thinner, it becomes less resistant to punctures and thus less able to perform its task of preventing accidental sticks. Therefore, a balance must be struck between these two competing goals when sheath 15 is designed. Of course, where this balance will fall will depend upon the characteristics of the materials used to make sheath 15. Currently, the inventors contemplate using plastic, Teflon®, or a metal such as braided stainless steel. However, other acceptable rigid or semi-rigid substances may be available now or developed in the future which may affect the thickness of sheath 15. Furthermore, it is anticipated that a non-rigid substance such as soft rubber which relies on needle 9 for its rigidity during insertion would perform adequately as a substance from which sheath 15 might be constructed. Sheath 15 may also be made from the same material as shroud 4 such that sheath 15 and shroud 4 could be constructed at the same time.

When sheath 15 is to be hypodermically insertable, the thickness of sheath 15 will also vary with the size of needle 9. Needles come in twenty five standard gauges, where gauge is a measure of external diameter 26. Standard needles range from 30 gauge which has an external diameter of $12/1000$ of an inch to 6 gauge which has an external diameter of $200/1000$ of an inch. The incremental change in diameter between gauges is not uniform. For example, 29 gauge has a diameter of $13/1000$ of an inch, only $1/1000$ more than 30 gauge. At the other end of the spectrum, 7 gauge has an outer diameter of $180/1000$ of an inch, $20/1000$ less than 6 gauge.

Although safety syringe 1 may be used with any size needle 9, needles in the middle of the standard needle range –24 or 25 to 18 or 19 gauge and preferably about 22 gauge—are expected to be used most often. A 24 gauge needle has an external diameter of $22/1000$ while 18 gauge is $50/1000$. When needle 9 falls into this middle range, it is anticipated that sheath 15, or at least tip end 16, should have an external diameter 27 of not more than about 150% of external diameter 26 of needle 9. In this size range, it is anticipated that the external diameter 27 of sheath 15, or at least tip end 16, should preferably be between about 118% and about 125% of external diameter 26 of needle 9. With larger needles 9, such as 6 or 7 gauge, it is expected that sheath 15 or tip end 16 should have an external diameter 27 of not more than about 133% and preferably about 110% of external diameter 26 of needle 9. It should be appreciated that the construction and composition of sheath 15 may allow it to be made thinner than the ranges given above in furtherance of the goal of patient comfort. Similarly, different construction and composition may force sheath 15 to be thicker in order to satisfy the goal of puncture resistance. Additional information regarding the construction of sheath 15 and/or needle 9 may be found in U.S. Pat. Nos. 5,460,611, 5,720,727, 5,785,662, 5,846,228, 5,964,735, 5,993,418, and PCT Applications US95/11426 and US97/09140, all of which are hereby incorporated by reference in their entirety to the extent they are not contrary to the teachings herein.

Shroud 4 and sheath 15 will most preferably be manufactured of plastic by injection molding. Needle 9 will preferably be a standard stainless steel double ended needle containing the male threads of Luer Lock 12 such as are commercially available from the Becton Dickinson company of Franklin Lakes, N.J. under their VACUTAINER® trademark. The preferred vacuum specimen tube 2 and stopper 3 are also commercially available from Becton Dickinson under the same trademark.

It is anticipated that needle 9, sleeve 13, and sheath 15 will be provided in a preassembled needle assembly 28. Needle assembly will preferably also include a cap 29 having a first half 29A designed to fit over first end 10 of needle 9 and sheath 15 and a second half 29B designed to fit over second end 11 of needle 9 and sleeve 13. Safety syringe 1 may be assembled by removing second half 29B of cap 29 and using first half 29A to handle needle assembly 28. After needle 9 and sheath 15 have been threaded onto Luer lock 12, first half 29A of cap 29 may be removed leaving safety syringe 1 ready for use. Sheath 15 should be in exposed position 18 when first half 29A is removed.

In operation, assuming blood is being drawn from a vein, needle 9 will be injected into the patient's vein, and sheath 15, or at least tip end 16 of sheath 15, will be injected with needle 9. If clear sleeve 13 is used, the operator will be able to tell that the vein has been found because blood will be visible in sleeve 13. When needle 9 is in the vein, vacuum specimen tube 2 will be inserted into shroud chamber 8 via second end 6. Stopper 3 of vacuum specimen tube 2 will encounter tube end 21 of arm 19 as vacuum specimen tube 2 approaches first end 5 of shroud 4. As vacuum specimen tube 2 is advanced further, stopper 3 will move sheath 15, via arm 19, from exposed position 18 to covered position 17. Stopper 3 will also move tube end 21 into engagement with recess 25, thereby locking sheath 15 in covered position 17. Stopper 3 will also encounter second end 11 of needle 9 and sleeve 13 as vacuum specimen tube 2 is advanced. When stopper 3 is pressed against second end 11 of needle 9, the sharp point of second end 11 will pierce sleeve 13 and stopper 3. Continued advancement of vacuum specimen tube 2 will push sleeve 13 back toward first end 5 of shroud 4 and will push second end 11 of needle 9 through stopper 3. When second end 11 of needle 9 has gone completely through stopper 3, needle 9 will fluidly connect vacuum specimen tube 2 and the vein. The vacuum in tube 2 will cause blood to flow through needle 9 into vacuum specimen tube 2. When vacuum specimen tube 2 is full, it may be removed simply by pulling it off second end 11 of needle 9. As vacuum specimen tube 2 is removed, sleeve 13 will return to its original position covering second end 11 of needle 9. If more blood is desired, another vacuum specimen tube 2 may be inserted into shroud 4 and the foregoing procedure repeated, except that sheath 15 will remain in covered position 17 for the remainder of the process. Sleeve 13 will prevent blood from flowing though needle 9 when no vacuum specimen tube 2 is in place. When blood collection is complete, syringe 1 may be removed from the patient. When it is removed, sheath 15 will already be locked in covered position 17, eliminating the possibility of an accidental stick.

It is anticipated that these and other uses and embodiments will be apparent to those skilled in the art from the foregoing description and drawings and are intended to be covered by the scope of the following claims.

We claim:

1. A fluid collection safety syringe for use with at least one vacuum specimen tube sealed with a pierceable cover, said syringe comprising:

a substantially hollow shroud having a first end, a second end, and sidewalls extending between said first end and said second end, said sidewalls, said first end and said second end defining a shroud chamber, said shroud chamber sized to receive said vacuum specimen tube;

a needle having a first end and a second end, said needle mounted in said first end of said shroud such that said first end of said needle is outside said shroud chamber and said second end of said needle is inside said shroud chamber, said first end of said needle having a point configured to allow said first end of said needle to be hypodermically inserted into a patient, said second end of said needle configured to pierce said cover of said vacuum tube when said vacuum specimen tube is positioned within said shroud chamber and advanced toward said first end of said shroud; and a sheath slidably disposed over said first end of said needle, said sheath having a tip end, wherein at least said tip end of said sheath is sized to be hypodermically insertable with said first end of said needle, said sheath having an exposed position wherein said point of said first end of said needle is outside said sheath, said sheath also having a covered position wherein said point of said first end of said needle is inside said sheath, said sheath configured to be advancable from said exposed position to said covered position after said first end of said needle and said tip end of said sheath have been hypodermically inserted into said patient.

2. A fluid collection safety syringe according to claim 1 wherein said sheath is configured to move from said exposed position to said covered position as said vacuum specimen tube is advanced toward said first end of said barrel.

3. A fluid collection safety syringe according to claim 1 further comprising an arm extending from said sheath, said arm having a tube end opposite said sheath, said tube end extending to within said shroud chamber when said sheath is in said exposed position, said tube end of said arm positioned to engage said vacuum specimen tube as said vacuum specimen tube is advanced toward said first end of said shroud, whereby said sheath may be moved from said exposed position to said covered position.

4. A fluid collection safety syringe according to claim 3 wherein said tube end of said arm is wider than said arm.

5. A fluid collection safety syringe according to claim 4 wherein said first end of said tube contains a curved slot having a wide end sized to permit passage of said arm and said tube end of said arm, said slot also having a narrow end sized to prevent passage of said tube end of said arm.

6. A fluid collection safety syringe according to claim 4 wherein said sidewalls are configured to engage said tube end of said arm when said sheath is in said covered position, whereby said sheath may be locked in said covered position.

7. A fluid collection safety syringe according to claim 6 wherein said sidewalls contain a recess sized and positioned to engage said tube end of said arm when said sheath is in said covered position.

8. A fluid collection safety syringe according to claim 1 further comprising a collapsible sleeve sealably mounted over said second end of said needle.

9. A fluid collection safety syringe according to claim 8 wherein said second end of said needle has a point configured to pierce said collapsible sleeve when said collapsible sleeve is pressed against said point.

10. A fluid collection safety syringe according to claim 8 wherein said sleeve is substantially clear.

11. A fluid collection safety syringe according to claim 10 wherein said sleeve contains a reservoir tip sufficient to receive a small amount of fluid from said second end of said needle.

12. A fluid collection safety syringe for use with at least one vacuum specimen tube sealed with a pierceable cover, said syringe comprising:

a substantially hollow shroud having a first end, a second end, and sidewalls extending between said first end and said second end, said sidewalls, said first end and said second end defining a shroud chamber, said shroud chamber sized to receive said vacuum specimen tube;

a needle having a first end and a second end, said needle mounted in said first end of said shroud such that said first end of said needle is outside said shroud chamber and said second end of said needle is inside said shroud chamber, said first end of said needle having a point configured to allow said first end of said needle to be hypodermically inserted into a patient, said second end of said needle configured to pierce said cover of said vacuum tube when said vacuum specimen tube is positioned within said shroud chamber and advanced toward said first end of said shroud;

a sheath slidably disposed over said first end of said needle, said sheath having a tip end, wherein at least said tip end of said sheath is sized to be hypodermically insertable with said first end of said needle, said sheath having an exposed position wherein said point of said first end of said needle is outside said sheath, said sheath also having a covered position wherein said point of said first end of said needle is inside said sheath, said sheath configured to be advancable from said exposed position to said covered position after said first end of said needle and said tip end of said sheath have been hypodermically inserted into said patient; and an arm extending from said sheath, said arm having a tube end opposite said sheath, said tube end extending to within said shroud chamber when said sheath is in said exposed position, said tube end of said arm positioned to engage said vacuum specimen tube as said vacuum specimen tube is advanced toward said first end of said shroud, whereby said sheath may be moved from said exposed position to said covered position.

13. A fluid collection safety syringe according to claim 12 wherein said tube end of said arm is wider than said arm.

14. A fluid collection safety syringe according to claim 13 wherein said first end of said tube contains a curved slot having a wide end sized to permit passage of said arm and said tube end of said arm, said slot also having a narrow end sized to prevent passage of said tube end of said arm.

15. A fluid collection safety syringe according to claim 13 wherein said sidewalls are configured to engage said tube end of said arm when said sheath is in said covered position, whereby said sheath may be locked in said covered position.

16. A fluid collection safety syringe according to claim 15 wherein said sidewalls contain a recess sized and positioned to engage said tube end of said arm when said sheath is in said covered position.

17. A fluid collection safety syringe according to claim 12 further comprising a collapsible sleeve sealably mounted over said second end of said needle.

18. A fluid collection safety syringe according to claim 17 wherein said second end of said needle has a point configured to pierce said collapsible sleeve when said collapsible sleeve is pressed against said point.

19. A fluid collection safety syringe according to claim 17 wherein said sleeve is substantially clear.

20. A fluid collection safety syringe according to claim 19 wherein said sleeve contains a reservoir tip sufficient to receive a small amount of fluid from said second end of said needle.

* * * * *